United States Patent [19]

Wagner

[11] 4,166,774
[45] Sep. 4, 1979

[54] ACRYLIC ACID RECOVERY AND PURIFICATION

[75] Inventor: David R. Wagner, Cleveland, Ohio

[73] Assignee: The Standard Oil Company

[21] Appl. No.: 857,147

[22] Filed: Dec. 5, 1977

[51] Int. Cl.² .................. C07C 57/04; B01D 3/36; C07C 51/44
[52] U.S. Cl. ...................... 203/82; 203/16; 203/57; 203/69; 203/70; 203/74; 203/75; 203/81; 203/DIG. 19; 203/DIG. 21; 562/600; 562/608
[58] Field of Search .......... 260/533 N, 530 N, 526 N; 203/39–46, DIG. 21, 99, 15, DIG. 19, 98, 75, 82, 83, 85, 76, 79; 562/600, 608

[56] References Cited
U.S. PATENT DOCUMENTS

| 2,309,653 | 2/1943 | Leum et al. | 203/99 |
| 3,073,752 | 1/1963 | Mention | 203/83 |
| 3,210,271 | 10/1965 | Byerly et al. | 203/82 |
| 3,219,547 | 11/1965 | Wheeler | 203/99 |
| 3,399,120 | 8/1968 | Lovett | 203/85 |
| 3,433,831 | 3/1969 | Yomiyama et al. | 260/526 N |
| 3,445,345 | 5/1969 | Katzen et al. | 203/85 |
| 3,692,636 | 9/1972 | Huguet | 203/99 |
| 3,725,211 | 4/1973 | Gehrken et al. | 203/99 |
| 3,769,177 | 10/1973 | Eubanks et al. | 203/99 |
| 3,990,952 | 11/1976 | Katzen et al. | 203/85 |

Primary Examiner—Wilbur L. Bascomb, Jr.
Attorney, Agent, or Firm—David J. Untener; Herbert D. Knudsen; Larry W. Evans

[57] ABSTRACT

The separation of acrylic acid from a mixture of acrylic acid and acetic acid found in the reaction product stream obtained in the process of producing acrylic acid by the oxidation of propylene or acrolein is improved by removing a vapor sidestream from the solvent recovery column found in the process. Acetic acid is then separated from this stream without the addition of external heat.

9 Claims, 2 Drawing Figures

ACRYLIC ACID RECOVERY AND PURIFICATION

BACKGROUND OF THE INVENTION

Acrylic acid is produced from the vapor phase oxidation of propylene or acrolein over an oxidation catalyst. The gaseous reactor effluent is then cooled and/or absorbed in water to obtain an aqueous solution containing from 10–80% acrylic acid, acetic acid, and various impurities.

The separation of acrylic acid from this aqueous stream has been difficult due to the relative volatilities of acrylic acid, acetic acid and water, which prevents simple fractional distillation.

Several different processes have been proposed to perform this separation. For example, U.S. Pat. No. 3,830,707 discloses a process wherein a specific entrainer of isooctane or nitroethane is used to perform an azeotropic distillation. The entrainer allows the removal of acetic acid and water overhead, while substantially purified acrylic acid is removed as a bottoms product. Other entrainers that have been proposed have also included benzene and toluene.

Another method for separation of acrylic acid has been by solvent extraction. The acrylic acid, acetic acid and water are extracted from the aqueous solution by countercurrent extraction. Many different types of solvents have been proposed for this extraction, some of which may also be used as entrainers. Among typical extraction solvents have been phosphates; aliphatic or aromatic hydrocarbons; ethers such as diphenol ether; alcohols and esters. U.S. Pat. No. 3,859,175, although directed to a dual solvent system for entrainment, discloses as prior art the extraction of acrylic acid using a solvent mixture of methylethyl ketone and either a xylene or ethyl benzene. Typically, such solvent extraction systems can be divided into those solvents that have a boiling point higher than acrylic acid and those that boil at a temperature lower than the boiling point of acrylic acid.

A third method for recovery of acrylic acid has been the combination of extraction followed by entrainment such as found in U.S. Pat. No. 3,433,831.

A principal disadvantage with recovery systems using solvents that have a boiling point lower than that of acrlylic acid has been the need for a large amount of heat usage in performing the separation. The present invention has discovered a method for both reducing the size of the final column needed in the separation process and in eliminating the heat necessary for this final separation.

SUMMARY OF THE INVENTION

It has been discovered that capital cost reduction and energy savings may be obtained in the process for the recovery of acrylic acid from an aqueous solution containing 10–80% acrylic acid resulting from the oxidation of propylene or acrolein wherein the acrylic acid and acetic acid is extracted with a solvent boiling below the boiling point of acrylic acid, the extractant containing solvent, acrylic acid, acetic acid and water is distilled in a solvent recovery column to obtain an overhead stream of solvent and water, and a bottoms stream of acrylic acid, the improvement comprising removing a vapor stream from below the feed tray of the solvent recovery column and rectifying said vapor stream to remove acetic acid.

The invention may also be stated as comprising the steps of:

(a) separating with a solvent an aqueous solution obtained from the process of oxidation of propylene or acrolein to obtain a first overhead stream of solvent, acrylic acid, acetic acid and water;

(b) distilling said first stream in a solvent recovery column having distillation trays to obtain a second overhead stream of solvent and water and a bottoms stream of acrylic acid;

(c) removing a vapor stream from below the feed tray of the solvent recovery column, said vapor stream containing acrylic acid and acetic acid;

(d) rectifying said vapor stream to separate acetic acid.

The invention may best be understood by reference to the drawings.

DESCRIPTION OF THE DRAWINGS

Referring to FIG. 1, the aqueous solution obtained in the process for production of acrylic acid from the oxidation of propylene or acrolein is passed through line 100 to extraction column 102. A solvent enters the extraction column at the bottom through line 104 and contacts the aqueous solution countercurrently to extract the acrylic acid. The extract, comprising the solvent, acrylic acid, acetic acid and water leaves the extraction column through line 106 and is sent to a solvent recovery column 110. The residue not extracted, being various impurities, dissolved solvent and water leaves the extraction column through line 108.

In the solvent recovery column 110 distillation is performed. Heat is added to the column through exchanger 120. A vapor stream of solvent and water leaves the solvent recovery column in line 112 and is passed to condenser 114. Here the solvent and water are condensed, a portion being returned to the solvent recovery column through line 116 as reflux. The remaining solvent and water is returned to the extraction column through line 104 for reuse. Acetic acid, acrylic acid and a minor amount of solvent leaves the solvent recovery column through line 118 and passes to final separation column 122. Herein another distillation is performed with heat being added to the column through exchanger 134. A vapor stream is removed overhead through line 124 that contains acetic acid. This vapor stream is condensed in condenser 126 and the condensed liquid can be recycled back to the column through line 128 or a portion removed from the system through line 130. Substantially purified acrylic acid is removed from the final separation column through line 132.

Figure 1:
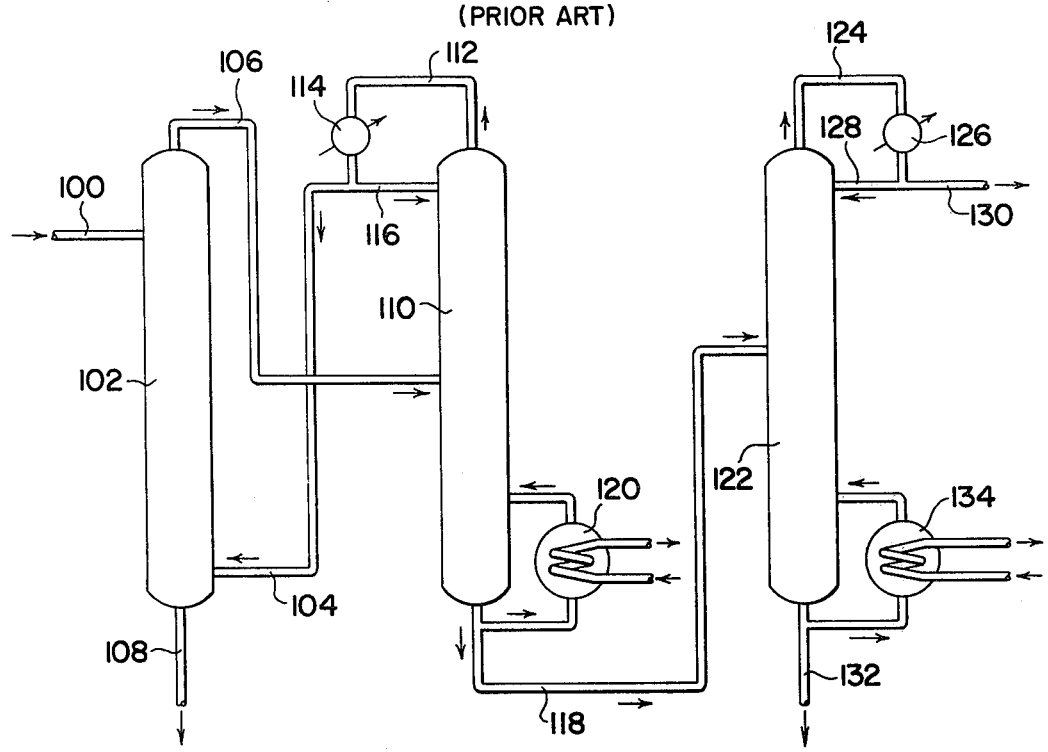
FIG. 1 shows the prior art method of separating acrylic acid by extraction.
Figure 2:
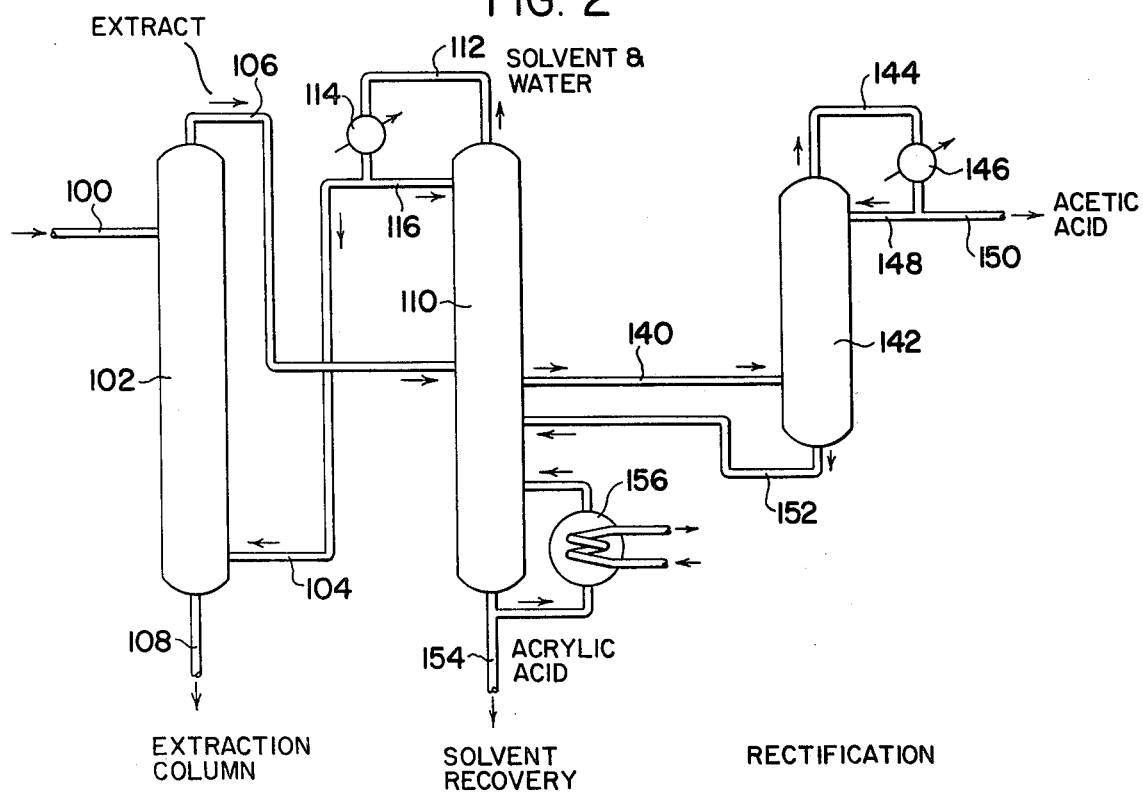
FIG. 2 shows one embodiment of the present invention.

FIG. 2, being an embodiment of the present invention, shows the advantages over the prior art. The numbers of the various streams and equipment which are the same as FIG. 1 have been maintained. Referring specifically to the solvent recovery column 110, it can be seen that the solvent and water are removed overhead through line 112 to condenser 114 as in the previous figure. However, a vapor sidestream is removed through line 140 and passed to a much smaller column 142. Without the addition of heat, acetic acid passes overhead and is removed from the column through line 144. This overhead stream then is sent to condenser 146 and the condensed liquid is both used as reflux through line 148 back to the column, and removed from the system through line 150. The bottoms stream of column 142 contains acrylic acid and acetic acid. This stream is returned to the solvent recovery column through line 152. Acrylic acid is removed from the solvent recovery column bottoms through line 154. A portion is sent to indirect heat exchange in exchanger 156 to provide the heat necessary to reboil the column.

It can thus be seen that acetic acid can be separated from acrylic acid in a much smaller process requiring less energy.

DESCRIPTION OF THE PREFERRED EMBODIMENT

It is preferred that the invention be used with those recovery systems that use a solvent for extraction of acrylic acid, acetic acid and water.

The solvents used in the present invention are those known in the art that can extract acrylic acid. The solvent must have an azeotropic boiling point with water below the boiling point of acrylic acid. This is required so that the solvent and water can be removed overhead in the solvent recovery column. There are many solvents that meet this requirement, such as those mentioned in U.S. Pat. No. 3,478,093. These include, to name a few, benzene, diosopropyl ether and toluene. The solvent may also be a combination of two or more solvents such as described in U.S. Pat. No. 3,433,831.

In a second embodiment, the present invention is also applicable to entrainment recovery systems wherein distillation with a solvent is performed in the first column rather than extraction. In this process, the overhead stream from the distillation column will contain solvent, acetic acid, water and some acrylic acid.

The operating parameters and relative construction of the first column depends on whether the process uses extraction or entrainment, and the specific type of solvent. Typically, this column is operated at atmospheric or subatmospheric conditions. One of skill in the art is aware of the various column designs based on specific solvents.

Principal to the present invention is the solvent recovery column. This column performs distillation necessary to recover and recycle solvent for further use. Again, the exact column design will depend on the type of solvent used and the composition of the extract or entrained liquid from the first column.

The extract is normally fed to the upper half of the solvent recovery column. This column performs the distillation, usually at pressures from about 100 to about 400 mm Hg. The lower pressures allow lower temperatures to be used in the distillation, thus preventing undesirable polymerization of the acrylic acid.

The overhead stream from the solvent recovery column contains solvent and water. This vapor stream is then condensed. A portion is recycled to the solvent recovery column as reflux, while the remainder is returned to the extraction or entrainment column for solvent reuse.

It has been discovered that the concentration of acetic acid in the solvent recovery column reaches a maximum below the feed tray. Specifically, this maximum occurs between ¼ to ½ of the number of trays in the column. By removing the vapors at this point in the column, the acetic acid may be separated from the acrylic acid without the application of additional heat. Further, the number of trays necessary for this separation is greatly reduced.

The vapor stream is passed to a small rectification column, typically having four to about twelve trays. Acetic acid is removed as a vaporous overhead, condensed and removed from the system. A portion of this condensed liquid is returned to the column as reflux. The bottoms stream of this small rectifying column, being acrylic acid and acetic acid, is returned to the solvent recovery column at a point below the vapor removal.

The vapor stream may also contain some solvent. This solvent, if present, will then appear in the vaporous overhead of the rectification column. If pure acetic acid is desired, this vaporous overhead should be passed to another column for solvent separation.

By using the present invention, the size of the final column for separation of acetic acid from acrylic acid is greatly reduced. Further, the various equipment necessary to reboil this column has been eliminated. Although somewhat more heat may be required in the solvent recovery column, the total amount of heat necessary to perform the complete operation of solvent recovery and acetic acid separation is substantially reduced.

EXAMPLE

An aqueous solution obtained from the oxidation reaction of propylene, comprising approximately 55 wt.% acrylic acid, water, acetic acid and some impurities is sent to the top of a first column. In this column, the aqueous stream is contacted countercurrently with diisopropyl ether having a boiling point of 67.5° C. The extract is removed overhead and has the following composition:

| Component | Wt. % |
|---|---|
| Acrylic Acid | 19 |
| Acetic Acid | 1 |
| Solvent | 76 |
| Water | 3 |
| Impurities | 1 |

This stream is passed to the 15th stage of a solvent recovery column having 19 distillation stages. The bottom of the column is reboiled to provide the heat necessary for distillation. An overhead stream containing all of the solvent, water and about 10% of the acetic acid is removed and condensed in a condenser. A portion of the condensed liquid is used for reflux, the remainder being recycled back to the extraction column.

A vapor stream is removed from the 7th stage of the solvent recovery column. This vapor stream has a composition of about 80% acrylic acid and about 20% acetic acid. The vapor stream is then passed to the bottom of a column having four stages.

Without the addition of heat, acetic acid is removed overhead as a vapor stream. This stream is condensed, with a portion of the condensed liquid being used as reflux and the remainder removed from the system. Approximately 90% of the acetic acid contained in the feed to the solvent recovery unit is removed in this manner.

The bottoms of the small rectifying column, containing acetic acid and acrylic acid, is then returned to the 7th stage tray of the solvent recovery column.

By removing the acetic acid in this manner, a bottoms stream of 99.9% acrylic acid can be recovered from the solvent recovery column.

I claim:

1. A method for separating acrylic acid from an aqueous solution of acrylic acid and acetic acid comprising the steps of:
   (a) contacting the aqueous solution with a solvent in a first column to obtain a first overhead stream of solvent, acrylic acid, acetic acid and water;
   (b) distilling said first stream in a solvent recovery column having distillation trays, to obtain a second overhead stream of solvent and water, and a bottoms stream of acrylic acid;
   (c) removing a vapor stream from below the feed tray of the solvent recovery column, said vapor stream containing acrylic acid and acetic acid;
   (d) rectifying said vapor stream to separate and remove acetic acid.

2. The method of claim 1 wherein the solvent has a boiling point below that of acrylic acid.

3. The method of claim 2 wherein extraction is performed in the column of step (a).

4. The method of claim 2 wherein entrainment distillation is performed in the column of step (a).

5. The method of claim 2 wherein the vapor stream of step (c) is removed from a point between the bottom half and the bottom quarter of the solvent recovery column.

6. The method of claim 5 wherein the rectification of the vapor stream is accomplished in a second column having 3–10 trays.

7. The method of claim 6 wherein rectification is performed in the second column to obtain a third overhead stream of acetic acid and a bottoms stream of acrylic acid and acetic acid.

8. The method of claim 7 wherein the bottoms stream obtained from the rectification column is returned to the solvent recovery column.

9. In the process for the recovery of acrylic acid from an aqueous solution resulting from the oxidation of propylene or acrolein, wherein the acrylic acid, acetic acid and water is extracted with a solvent boiling below the boiling point of acrylic acid, the resultant extract is distilled in a solvent recovery column to obtain an overhead stream of solvent and water, and a bottoms stream of acrylic acid, the improvement comprising removing a vapor stream containing acrylic acid and acetic acid from below the feed tray of the solvent recovery column, and rectifying said vapor stream to remove acetic acid.

* * * * *